(12) United States Patent
Wada et al.

(10) Patent No.: US 11,318,484 B2
(45) Date of Patent: May 3, 2022

(54) NOZZLE AND DISPENSING CONTAINER

(71) Applicant: FUJIFILM Corporation, Tokyo (JP)

(72) Inventors: Atsuhiko Wada, Ashigarakami-gun (JP); Keiji Shigesada, Ashigarakami-gun (JP); Junichi Katada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/367,807

(22) Filed: Mar. 28, 2019

(65) Prior Publication Data

US 2019/0224693 A1 Jul. 25, 2019

Related U.S. Application Data

(63) Continuation of application No. PCT/JP2017/033346, filed on Sep. 14, 2017.

(30) Foreign Application Priority Data

Sep. 30, 2016 (JP) .............................. JP2016-193791

(51) Int. Cl.
*B05B 1/10* (2006.01)
*G01N 1/10* (2006.01)
(Continued)

(52) U.S. Cl.
CPC .............. *B05B 1/10* (2013.01); *B01L 3/0272* (2013.01); *B01L 3/0275* (2013.01);
(Continued)

(58) Field of Classification Search
CPC .......... B05B 1/10; G01N 33/543; G01N 1/00; G01N 1/10; G01N 33/54366;
(Continued)

(56) References Cited

U.S. PATENT DOCUMENTS 4,950,237 A * 8/1990 Henault ............. B65D 81/3211
604/82
5,221,027 A 6/1993 Gibilsco
(Continued)

FOREIGN PATENT DOCUMENTS

CN 1094164 A 10/1994
CN 202210043 U 5/2012
(Continued)

OTHER PUBLICATIONS

Japanese Office Action, dated Feb. 12, 2020, for corresponding Japanese Application No. 2018-542383, with an English machine translation.
(Continued)

*Primary Examiner* — Qingzhang Zhou
(74) *Attorney, Agent, or Firm* — Birch, Stewart, Kolasch & Birch, LLP

(57) ABSTRACT

A nozzle includes a mounting opening that is to be connected to an opening portion of a container, an outlet that jets liquid stored in the container, a side face that connects the mounting opening to the outlet, and a liquid storage portion that stores a part of the liquid stored in the container in the nozzle without jetting a part of the liquid from the outlet in a case where the liquid is to be jetted from the dispensing container, that is, in a case where the outlet faces downward in the direction of gravity.

10 Claims, 3 Drawing Sheets

(51) Int. Cl.
  *G01N 33/543* (2006.01)
  *B01L 3/02* (2006.01)
  *G01N 1/00* (2006.01)

(52) U.S. Cl.
  CPC .............. *B01L 3/0293* (2013.01); *G01N 1/00* (2013.01); *G01N 1/10* (2013.01); *G01N 33/543* (2013.01); *G01N 33/54366* (2013.01); *B01L 2300/0681* (2013.01); *B01L 2300/0832* (2013.01); *B01L 2300/0854* (2013.01); *B01L 2300/161* (2013.01); *B01L 2400/086* (2013.01)

(58) Field of Classification Search
  CPC .... B01L 3/0272; B01L 3/0275; B01L 3/0293; B01L 2400/086; B01L 2300/0854; B01L 2300/0681; B01L 2300/0832; B01L 2300/161
  See application file for complete search history.

(56) References Cited

U.S. PATENT DOCUMENTS

| | | | |
|---|---|---|---|
| 5,260,030 A | 11/1993 | Devaughn | |
| 5,514,341 A | 5/1996 | Urata et al. | |
| 8,770,448 B2* | 7/2014 | Wochele | B01L 3/0272 222/420 |
| 2013/0075431 A1 | 3/2013 | Wochele | |
| 2016/0100786 A1* | 4/2016 | Nishio | A61B 5/150755 600/578 |

FOREIGN PATENT DOCUMENTS

| | | |
|---|---|---|
| CN | 204522997 U | 8/2015 |
| CN | 204638220 U | 9/2015 |
| CN | 105358954 A | 2/2016 |
| EP | 0315440 A2 | 5/1989 |
| EP | 0500172 A1 | 8/1992 |
| EP | 3018464 A1 | 5/2016 |
| FR | 2431325 A1 | 2/1980 |
| JP | 2-4675 A | 1/1990 |
| JP | 6-14971 A | 1/1994 |
| JP | 2007-46959 A | 2/2007 |
| JP | 2007-315793 A | 12/2007 |
| JP | 2012-168051 A | 9/2012 |
| JP | 2015-128749 A | 7/2015 |
| JP | 2015-187592 A | 10/2015 |
| WO | WO 2013/073558 A1 | 5/2013 |

OTHER PUBLICATIONS

Extended European Search Report, dated Aug. 5, 2019, for European Application No. 17855763.3.

International Preliminary Report on Patentability and Written Opinion of the International Searching Authority(Forms PCT/IB/326, PCT/IB/373 and PCT/ISA/237), dated Apr. 11, 2019, for International Application No. PCT/JP2017/033346, with an English Translation of the Written Opinion.

International Search Report (Form PCT/ISA/210), dated Oct. 31, 2017, for International Application No. PCT/JP2017/033346, with an English translation.

"National Important Environmental Protection Practical Technique and Example Process Collection", Chinese Environmental Protection Industry Association, Chinese Environmental Science Publishment, Aug. 2006, p. 20.

Office Action and Search Report dated Dec. 10, 2020 in Chinese Patent Application No. 201780060714.3, with English translation.

European Communication pursuant to Article 94(3) EPC for corresponding European Application No. 17855763.3, dated Oct. 14, 2020.

* cited by examiner

NOZZLE AND DISPENSING CONTAINER

CROSS-REFERENCE TO RELATED APPLICATIONS

This application is a continuation application of International Application No. PCT/JP2017/033346, filed Sep. 14, 2017, the disclosure of which is incorporated herein by reference in its entirety. Further, this application claims priority from Japanese Patent Application No. 2016-193791, filed Sep. 30, 2016, the disclosure of which is incorporated herein by reference in its entirety.

BACKGROUND OF THE INVENTION

1. Field of the Invention

The present invention relates to a nozzle and a dispensing container that are particularly suitably used to dispense a liquid sample for immunochromatographic measurement.

2. Description of the Related Art

Since an immunochromatography among immunoassay methods is easy to operate and can perform measurement in a short time, the immunochromatography is generally frequently used. A competitive reaction or a sandwich reaction is widely used as an immune reaction used in the immunochromatography. A sandwich reaction is a main stream in the immunochromatography among them, and the following operation is performed to detect a material to be detected, which is formed of an antigen contained in a sample, in a typical example of the sandwich reaction.

First, fine particles, which are sensitized by an antibody against the antigen as the material to be detected, are fixed to a chromatographic carrier as solid fine particles or the antibody is directly fixed to the chromatographic carrier, so that a chromatographic carrier including reactive portions is manufactured. On the other hand, labeled fine particles are sensitized with an antibody, which can be specifically bound to the material to be detected, so that sensitized labeled fine particles are manufactured. The sensitized labeled fine particles are chromatographically moved on the chromatographic carrier together with the sample. The fixed antibody becomes a fixed reagent in the reactive portions formed on the chromatographic carrier due to the above-mentioned operation, and is specifically bound to the sensitized labeled fine particles through the antigen as the material to be detected. As a result, the presence/absence or levels of signals, which are to be generated in a case where the sensitized labeled fine particles are caught by the reactive portions, are determined by visual observation or a measuring device. Accordingly, the presence/absence or the amount of the material to be detected in the sample can be measured.

SUMMARY OF THE INVENTION

A method of adding a liquid sample, from which an antigen is extracted, by a spot nozzle while using a dispensing container for immunochromatographic measurement disclosed in, for example, JP2007-046959A is generally used as the immunochromatography. However, in a case where the amount of a liquid sample to be added to a chromatographic carrier is large, the liquid sample slides on the upper surface of the chromatographic carrier and does not flow on the chromatographic carrier. For this reason, there is a case where a defect, such as a reduction in sensitivity, may occur. Particularly, in a case where the amount of a liquid sample to be added is large in an immunochromatography where a signal amplification method is performed to avoid a problem (false negative) that an antigen is not detected due to low sensitivity, it is often the case that a defect where a signal is not normally amplified may occur.

Since there is such a problem, the amount of a liquid sample to be added to the chromatographic carrier is generally specified in the immunochromatography. However, since the addition of a liquid sample is manually performed in most cases, there is a case where the amount of a liquid sample to be added may be increased.

The invention has been made in consideration of the above-mentioned problem, and an object of the invention is to provide a nozzle having a structure where liquid stored in a container is not jetted by an amount equal to or larger than a predetermined amount and a dispensing container comprising the nozzle.

A nozzle of the invention includes a mounting opening to be connected to an opening portion of a container, an outlet jetting liquid stored in the container, and a side face connecting the mounting opening to the outlet. The nozzle comprises a liquid storage portion that is provided in an interior space of the nozzle and stores the liquid in a case where the liquid stored in the container is to be jetted.

Here, the "liquid storage portion" means a container-shaped structural portion that can store liquid in the nozzle without jetting liquid from the outlet in a case where liquid stored in the container is to be jetted, that is, in a case where the outlet faces downward in the direction of gravity. The "liquid storage portion" excludes a structure where the container-shaped structural portion capable of storing liquid is not provided and liquid merely adheres to the inside of the nozzle and remains in the nozzle in a case where the outlet faces downward in the direction of gravity.

It is preferable that the nozzle of the invention further comprises a tubular portion of which an inside communicates with the outlet and which extends toward the mounting opening from the side face and the liquid storage portion is a space formed between an outer surface of the tubular portion and an inner surface of the side face.

Further, it is preferable that the nozzle further comprises a guide structure portion provided on at least a part of an inner portion of the liquid storage portion and guiding the liquid in the liquid storage portion toward the outlet from the mounting opening.

In a case where the nozzle of the invention comprises the guide structure portion, the guide structure portion may be a rib that is formed on at least a part of the inner portion of the liquid storage portion, may be a groove that is formed on at least a part of the inner portion of the liquid storage portion, and may be a protrusion that is formed on at least a part of the inner portion of the liquid storage portion.

Furthermore, in a case where the nozzle of the invention comprises the guide structure portion, it is preferable that the guide structure portion is formed in a range from a position closer to the mounting opening than an end portion of the liquid storage portion facing the mounting opening to a position close to the outlet, in a direction toward the mounting opening from the outlet.

Moreover, an entirety of the nozzle may be made of a hydrophilic material, at least a part of a portion where the liquid storage portion is formed may be made of a hydrophilic material, and hydrophilization may be performed on at least a part of a portion where the liquid storage portion is formed.

Further, the nozzle may be mounted on the container that stores a liquid sample for immunochromatographic measurement as the liquid.

A dispensing container of the invention comprises a container and the nozzle of the invention.

According to the nozzle and the dispensing container of the invention, the nozzle comprises the liquid storage portion that is provided in the interior space of the nozzle and stores liquid in a case where the liquid stored in the container is to be jetted. Accordingly, since all the liquid stored in the container mounted on the nozzle is not jetted from the nozzle and a part of the liquid is stored in the liquid storage portion, the liquid stored in the container is not allowed to be jetted by an amount equal to or larger than a predetermined amount.

DESCRIPTION OF THE PREFERRED EMBODIMENTS

Figure 1:
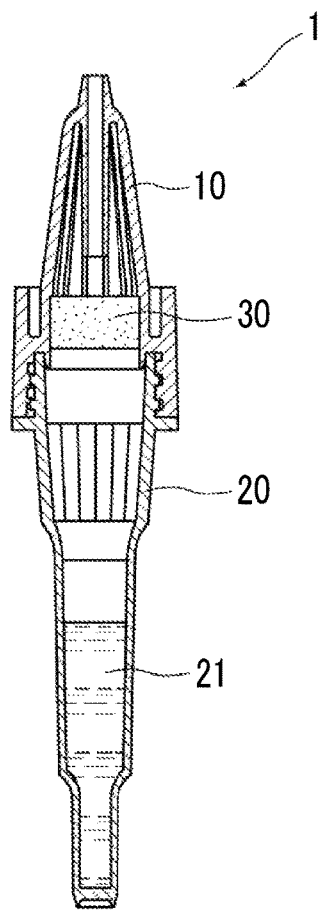
FIG. 1 is a cross-sectional view showing a preferred embodiment of a dispensing container of the invention.
Figure 4:
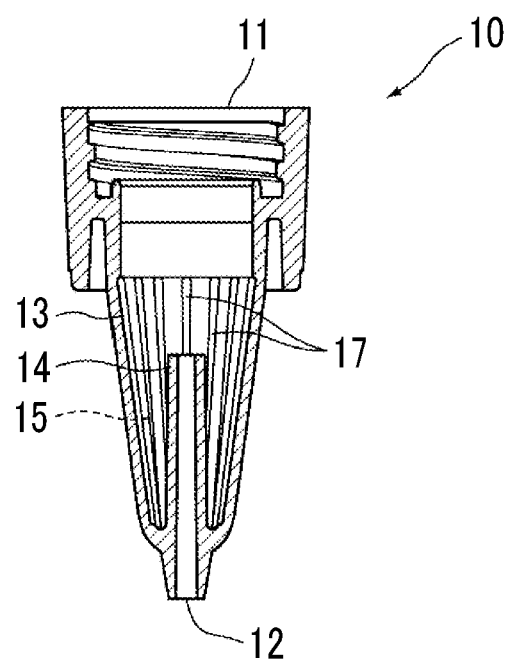
FIG. 4 is a cross-sectional view showing another aspect of the nozzle of the invention.
Figure 5:
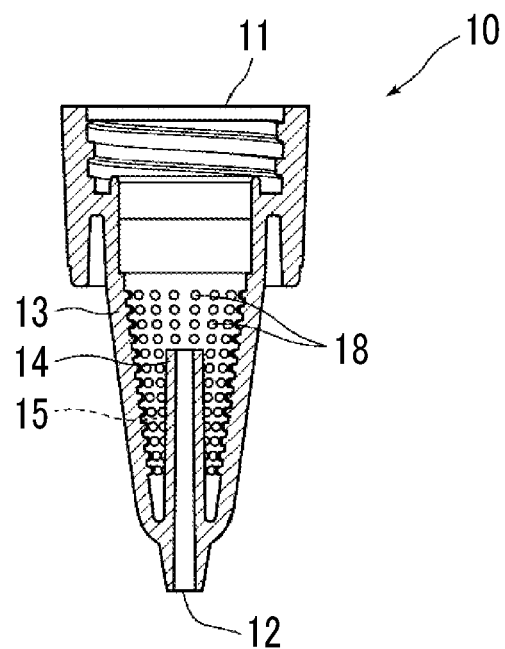
FIG. 5 is a cross-sectional view showing still another aspect of the nozzle of the invention.
Figure 6:
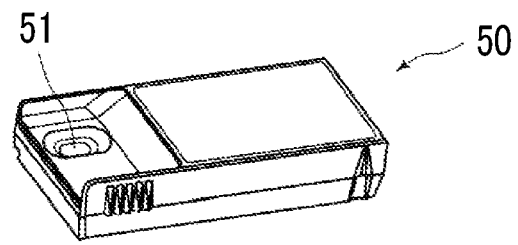
FIG. 6 is a perspective view of a test cartridge for immunochromatographic measurement to which a liquid sample is to be added by the dispensing container of the invention.

Embodiments of the invention will be described in detail below with reference to the drawings. FIG. 1 is a cross-sectional view showing a preferred embodiment of a dispensing container of the invention, FIG. 2 is a cross-sectional view of a nozzle of the dispensing container shown in FIG. 1, FIG. 3 is a top view of the nozzle shown in FIG. 2, FIG. 4 is a cross-sectional view showing another aspect of the nozzle of the invention, FIG. 5 is a cross-sectional view showing still another aspect of the nozzle of the invention, and FIG. 6 is a perspective view of a test cartridge for immunochromatographic measurement to which a liquid sample is to be added by the dispensing container of the invention.

As shown in FIG. 1, a dispensing container 1 of this embodiment is a dispensing container for immunochromatographic measurement and includes a container 20 that stores a liquid sample 21 for immunochromatographic measurement, a nozzle 10 that is mounted on the container 20, and a filter 30 that is disposed in the nozzle 10.

Figure 2:
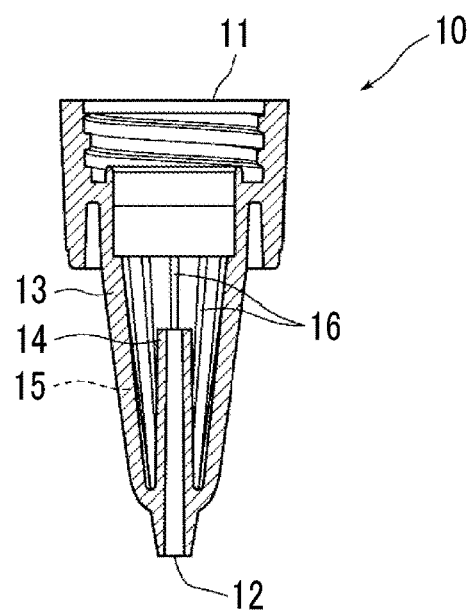
FIG. 2 is a cross-sectional view of a nozzle of the dispensing container shown in FIG. 1.
Figure 3:
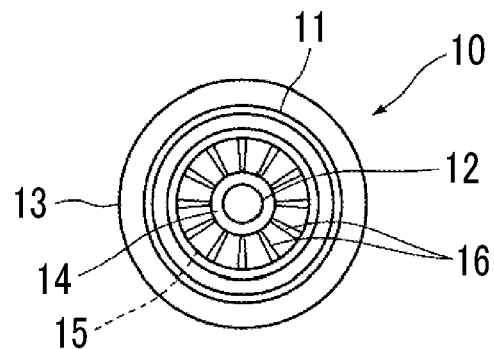
FIG. 3 is a top view of the nozzle shown in FIG. 2.

As shown in FIGS. 2 and 3, the nozzle 10 comprises a mounting opening 11 that is to be connected to an opening portion of the container 20, an outlet 12 that jets the liquid sample 21 stored in the container 20, a side face 13 that connects the mounting opening 11 to the outlet 12, a tubular portion 14 of which the inside communicates with the outlet 12 and which extends toward the mounting opening 11 from the side face 13, and a liquid storage portion 15 that is formed between the outer surface of the tubular portion 14 and the inner surface of the side face 13. The liquid storage portion 15 is a structural portion that can store a part of the liquid sample 21, which is stored in the container 20, in the nozzle 10 without jetting a part of the liquid sample 21 from the outlet 12 in a case where the liquid sample 21 is to be jetted from the dispensing container 1, that is, in a case where the outlet 12 faces downward in the direction of gravity.

Further, a plurality of ribs (projections) 16 as a guide structure portion, which guides the liquid sample 21 in the liquid storage portion 15 toward the outlet 12 from the mounting opening 11, are formed on the inner surface of the side face 13. The guide structure portion is a structural portion that guides the liquid sample 21 to an end portion of the liquid storage portion 15, which faces the outlet 12, from an inlet of the liquid storage portion 15 (an end portion of the liquid storage portion 15 facing the mounting opening 11) provided in the nozzle 10 by using the surface tension of the liquid sample 21.

Grooves 17 shown in FIG. 4 may be used as the guide structure portion instead of the ribs 16, or protrusions 18 shown in FIG. 5 may be used as the guide structure portion. Further, the grooves and the protrusions may be combined with each other. Furthermore, a position where the guide structure portion is to be formed is also not limited to the inner surface of the side face 13, and the guide structure portion may be formed on the outer surface of the tubular portion 14 or may be formed on both the inner surface of the side face 13 and the outer surface of the tubular portion 14.

Since the inlet of the liquid storage portion 15 (the end portion of the liquid storage portion 15 facing the mounting opening 11) provided in the nozzle 10 is narrow, the liquid sample 21 is not infiltrated into the end portion of the liquid storage portion 15 facing the outlet 12 and may not be stored in the liquid storage portion 15. However, since the liquid sample 21 can be infiltrated into the end portion of the liquid storage portion 15 facing the outlet 12 in a case where the above-mentioned guide structure portion is provided, the liquid sample 21 can be effectively stored in the liquid storage portion 15.

It is preferable that the guide structure portion is formed in a range to a position close to the outlet 12 from a position closer to the mounting opening 11 than the end portion of the liquid storage portion 15 facing the mounting opening 11 in a direction toward the mounting opening 11 from the outlet 12. In a case where this aspect is employed, the liquid sample 21 can be more effectively infiltrated into the end portion of the liquid storage portion 15 facing the outlet 12.

Further, since the wettability of the wall surface of the liquid storage portion 15 is improved in a case where the entirety of the nozzle 10 is made of a hydrophilic material or at least a part of a portion where the liquid storage portion 15 is formed is made of a hydrophilic material, the liquid sample 21 can be more effectively infiltrated into the end portion of the liquid storage portion 15 facing the outlet 12. Here, the hydrophilic material means a material of which a contact angle with water is 70° or less. Examples of the hydrophilic material include polyethylene to which an anti-static agent, a surfactant, or the like is added.

Even though hydrophilization is performed on at least a part of a portion where the liquid storage portion 15 is formed instead of a case where the entirety of the nozzle 10 is made of a hydrophilic material or at least a part of a portion where the liquid storage portion 15 is formed is made of a hydrophilic material, the same effect as the above-mentioned effect can be obtained. Specifically, examples of the hydrophilization include a plasma treatment for improving the wettability of the surface of a molded article and coating for a hydrophilic material.

In the dispensing container for immunochromatographic measurement, a specimen and extraction liquid are mixed with each other to prepare a liquid sample 21 in the container 20. However, since the liquid sample 21 cannot be appropriately prepared if the amount of the extraction liquid is too small in this case, a certain amount of the extraction liquid is prepared. Specifically, 400 µL of the extraction liquid is prepared in the dispensing container 1 of this embodiment.

Further, the droplet (the amount of one droplet) of the liquid sample 21 to be jetted from the nozzle 10 is 20 µL. For example, the amount of the liquid sample 21, which is to be added to a sample supply portion (chromatographic carrier) 51 of a test cartridge 50 for immunochromatographic measurement shown in FIG. 6, is enough as 40 µL (two droplets).

However, since the addition of the liquid sample 21 to the test cartridge 50 from the dispensing container 1 is manually performed, there is a case where the amount of the liquid sample 21 to be added is increased. Specifically, since the amount of the liquid sample 21, which is to be lost by adhering to the filter 30 or the inside of the container 20, of 400 µL of the liquid sample 21 stored in the container 20 is about 150 µL, about 250 µL of the liquid sample 21 to the maximum is added to the test cartridge 50. In this case, the liquid sample 21 slides on the upper surface of the chromatographic carrier due to the excessive supply of the liquid sample 21 and does not flow on the chromatographic carrier. For this reason, there is a concern that a defect, such as a reduction in sensitivity, may occur.

To solve the above-mentioned problem, the dispensing container 1 of this embodiment is adapted so that the liquid storage portion 15 is provided in the nozzle 10 and a predetermined amount of the liquid sample 21 can be stored in the nozzle 10 without being jetted from the outlet 12 in a case where the liquid sample 21 is to be jetted from the dispensing container 1, that is, in a case where the outlet 12 faces downward in the direction of gravity. The capacity of the liquid storage portion 15 is 120 µL in this embodiment. That is, since the amount of the liquid sample 21, which is to be lost by adhering to the filter 30 or the inside of the container 20, of 400 µL of the liquid sample 21 stored in the container 20 is about 150 µL and the amount of the liquid sample 21 to be stored in the liquid storage portion 15 is 120 µL, only about 130 µL of the liquid sample 21 to the maximum is added to the test cartridge 50. For this reason, the above-mentioned defect, such as a reduction in sensitivity, can be suppressed.

The invention will be described in more detail below with reference to examples. A material, the amount of a material to be used, a ratio of a material, the contents of treatment, the procedure of treatment, and the like, can be appropriately changed without departing from the scope of the invention. Accordingly, the scope of the invention should not be interpreted in a limited way by the examples to be described below.

(1) Manufacture of Spot Nozzle 1-1: Example 1

A nozzle, which has substantially the same shape as the shape shown in FIG. 2 and includes a tubular portion 14 having a height of 9.3 mm but does not include the ribs 16 as a guide structure portion provided on the inner surface of the side face 13 of the nozzle, was injection-molded with polyethylene.

1-2: Example 2

A nozzle, which has the shape shown in FIG. 2 and includes a tubular portion 14 having a height of 9.3 mm and the ribs 16 as a guide structure portion provided on the inner surface of the side face 13 of the nozzle, was injection-molded with polyethylene.

1-3: Example 3

A nozzle, which has the shape shown in FIG. 2 and includes a tubular portion 14 having a height of 9.3 mm and the ribs 16 as a guide structure portion provided on the inner surface of the side face 13 of the nozzle, was injection-molded with hydrophilic polypropylene (containing 2% or less of J226EA-antioxidant manufactured by Prime Polymer Co., Ltd.).

1-4: Example 4

A nozzle, which has the shape shown in FIG. 2 and includes a tubular portion 14 having a height of 9.3 mm and the ribs 16 as a guide structure portion provided on the inner surface of the side face 13 of the nozzle, was injection-molded with polyethylene to which an antifogging agent (RIKEMASTER ESR381 manufactured by Riken Vitamin Co., Ltd.) is added.

1-5: Comparative Example 1

A nozzle, which has substantially the same shape as the shape shown in FIG. 2 but does not include a tubular portion 14 and the ribs 16 as a guide structure portion, was injection-molded with polyethylene.

(2) Manufacture of Container

A container in which a liquid sample can be enclosed and on which a nozzle can be mounted was manufactured with polyethylene by injection molding.

(3) Manufacture of Liquid Sample 30 g of tris(hydroxymethyl)aminomethane was dissolved in 1000 mL of Milli-Q water, 1 g of Tween80 was added to the mixture, and the pH of the mixture was then adjusted to 7.7, so that the mixture was manufactured as a liquid sample.

(4) Evaluation

400 µL of a liquid sample was enclosed in the container, each nozzle of Examples 1 to 4 and Comparative Example 1 was mounted on the container, the container was pressed by fingers to jet all the liquid sample stored in the container from the nozzle, and the amount of the liquid sample remaining in the nozzle was measured.

(5) Results

Results are shown in Table 1. Table 1 shows results that are obtained in a case where the measurement of (4) is performed ten times for every nozzle. Here, it is defined that the invention is effective in a case where 80 µL or 100 µL or more of the liquid sample remains in the nozzle after all the liquid sample stored in the container is jetted from the nozzle.

TABLE 1

| | Molding material | Liquid storage portion | Guide structure portion | Residual ratio of 80 μL or more | Residual ratio of 100 μL or more |
|---|---|---|---|---|---|
| Example 1 | Polyethylene | Including | Not including | 6/10 | 2/10 |
| Example 2 | Polyethylene | Including | Including | 10/10 | 8/10 |
| Example 3 | Hydrophilic polypropylene | Including | Including | 10/10 | 10/10 |
| Example 4 | Polyethylene to which antifogging agent is added | Including | Including | 10/10 | 10/10 |
| Comparative Example 1 | Polyethylene | Not including | Not including | 0/10 | 0/10 |

As understood from the comparison between Examples 1 to 4 and Comparative Example 1, it could be confirmed from the results of Table 1 that a residual ratio is improved since the tubular portion is provided to form the liquid storage portion in the interior space of the nozzle.

Further, as understood from the comparison between Example 1 and Examples 2 to 4, it could be confirmed that a residual ratio is further improved since the guide structure portion is provided on the inner surface of the side face of the nozzle.

Furthermore, as understood from the comparison between Example 2 and Examples 3 and 4, it could be confirmed that a residual ratio is further improved since the nozzle is made of a hydrophilic material. Accordingly, the reliable collection of the liquid sample in the nozzle succeeded.

The preferred embodiment and examples of the invention have been described above, but the invention is not limited to the above-mentioned aspects. It goes without saying that the invention may have various improvements and modifications without departing from the scope of the invention.

For example, the nozzle and the dispensing container of the invention are not limited to a use for immunochromatographic measurement, and may be used for any use.

Further, the structure of the liquid storage portion is not limited to a space between the outer surface of the tubular portion and the inner surface of the side face of the nozzle. As long as a part of the liquid stored in the container can be stored by the structural portion in the nozzle without being jetted from the outlet in a case where liquid stored in the container is to be jetted from the dispensing container, that is, in a case where the outlet faces downward in the direction of gravity, any structure, such as a space partitioned by a plate-like partition in the interior space of the nozzle, may be employed for the liquid storage portion.

EXPLANATION OF REFERENCES

1: dispensing container
10: nozzle
11: mounting opening
12: outlet
13: side face
14: tubular portion
15: liquid storage portion
16: rib
17: groove
18: protrusion
20: container
21: liquid sample
30: filter
50: test cartridge
51: sample supply portion

What is claimed is:

1. A nozzle that comprises a mounting opening to be connected to an opening portion of a container, an outlet jetting liquid stored in the container, and a side face connecting the mounting opening to the outlet, the nozzle comprising:
a liquid storage portion that is provided in an interior space of the nozzle and stores the liquid in a case where the liquid is to be jetted,
a tubular portion of which an inside communicates with the outlet and which extends toward the mounting opening from the side face,
wherein the liquid storage portion is a space that is formed between an outer surface of the tubular portion and an inner surface of the side face and tapered toward the outlet, and
a guide structure portion that is provided on at least a part of an inner portion of the liquid storage portion and guides the liquid in the liquid storage portion toward the outlet from the mounting opening,
the guide structure portion being arranged circumferentially on the inner surface of the outlet and along an axial direction of the tubular portion.

2. The nozzle according to claim 1,
wherein the guide structure portion is a rib that is formed on at least a part of the inner portion of the liquid storage portion.

3. The nozzle according to claim 1,
wherein the guide structure portion is a groove that is formed on at least a part of the inner portion of the liquid storage portion.

4. The nozzle according to claim 1,
wherein the guide structure portion is a protrusion that is formed on at least a part of the inner portion of the liquid storage portion.

5. The nozzle according to claim 1,
wherein the guide structure portion is formed in a range from a position closer to the mounting opening than an end portion of the liquid storage portion facing the mounting opening to a position close to the outlet, in a direction toward the mounting opening from the outlet.

6. The nozzle according to claim 1,
wherein an entirety of the nozzle is made of a hydrophilic material.

7. The nozzle according to claim 1,
wherein at least a part of a portion where the liquid storage portion is formed is made of a hydrophilic material.

8. The nozzle according to claim 1,
wherein hydrophilization is performed on at least a part of a portion where the liquid storage portion is formed.

9. The nozzle according to claim 1,
wherein the nozzle is mounted on the container that stores a liquid sample for immunochromatographic measurement as the liquid.

10. A dispensing container comprising:
a container; and
the nozzle according to claim 1.

* * * * *